US008581454B2

(12) United States Patent
Corrington et al.

(10) Patent No.: US 8,581,454 B2
(45) Date of Patent: Nov. 12, 2013

(54) HANDHELD DEVICE WITH THERMAL PADDING

(75) Inventors: Richard A. Corrington, San Clemente, CA (US); Francis James Steinmetz, Whittier, CA (US); Daniel Manuel Santos, Laguna Niguel, CA (US)

(73) Assignee: Pro-Dex, Inc., Irvine, CA (US)

( * ) Notice: Subject to any disclaimer, the term of this patent is extended or adjusted under 35 U.S.C. 154(b) by 425 days.

(21) Appl. No.: 13/004,745

(22) Filed: Jan. 11, 2011

(65) Prior Publication Data
US 2011/0213395 A1 Sep. 1, 2011

Related U.S. Application Data

(60) Provisional application No. 61/293,986, filed on Jan. 11, 2010.

(51) Int. Cl.
*H02K 9/00* (2006.01)
(52) U.S. Cl.
USPC ................... 310/52; 310/50; 310/54
(58) Field of Classification Search
USPC ............. 310/50, 52, 54, 58, 64, 89, 91
See application file for complete search history.

(56) References Cited

U.S. PATENT DOCUMENTS

| 5,383,785 A | 1/1995 | Brugger |
| 5,431,675 A | 7/1995 | Nicholas et al. |
| 5,520,634 A | 5/1996 | Fox et al. |
| 5,658,304 A | 8/1997 | Lim |
| 5,676,680 A | 10/1997 | Lim |
| 5,729,904 A | 3/1998 | Trott |
| 5,839,196 A | 11/1998 | Trott |
| 5,868,785 A | 2/1999 | Tal et al. |
| 5,871,493 A | 2/1999 | Sjostrom et al. |
| 6,162,214 A | 12/2000 | Mueller et al. |
| 6,302,406 B1 | 10/2001 | Ventura |
| 6,312,441 B1 | 11/2001 | Deng |
| 6,432,119 B1 | 8/2002 | Saadat |
| 6,623,500 B1 | 9/2003 | Cook et al. |
| 6,656,133 B2 | 12/2003 | Voegele et al. |
| 6,727,611 B2 * | 4/2004 | Bostwick ..................... 310/58 |

(Continued)

FOREIGN PATENT DOCUMENTS

EP 0830846 A 3/1998
EP 0 905 432 A2 3/1999

(Continued)

OTHER PUBLICATIONS

International Search Report and Written Opinion from corresponding International Application No. PCT/US2011/020884, mailed Mar. 29, 2011, 9 pages.

(Continued)

*Primary Examiner* — Nguyen N Hanh
(74) *Attorney, Agent, or Firm* — Knobbe, Martens, Olson & Bear, LLP

(57) ABSTRACT

A handheld device comprises a housing, a motor, and a thermally conductive pad disposed in a space between the motor and the housing. Heat generated by the motor can be conducted by the thermal pad to the housing or to an internal fluid passage generally extending the length of the motor. In some embodiments, the thermal pad is configured to maintain the temperature of the housing in accordance with industry guidelines.

17 Claims, 2 Drawing Sheets

(56) References Cited

U.S. PATENT DOCUMENTS

| | | |
|---|---|---|
| 6,780,189 B2 | 8/2004 | Tidwell et al. |
| 6,809,508 B2 | 10/2004 | Donofrio |
| 6,945,981 B2 | 9/2005 | Donofrio et al. |
| 6,958,071 B2 | 10/2005 | Carusillo et al. |
| 6,977,495 B2 | 12/2005 | Donofrio |
| 7,011,661 B2 | 3/2006 | Riedel et al. |
| 7,025,732 B2 | 4/2006 | Thompson et al. |
| 7,226,424 B2 | 6/2007 | Ritchart et al. |
| 7,237,990 B2 | 7/2007 | Deng |
| 7,990,005 B2 * | 8/2011 | Walter et al. .............. 310/89 |
| 2001/0047183 A1 | 11/2001 | Privitera et al. |
| 2002/0040229 A1 | 4/2002 | Norman |
| 2003/0225411 A1 | 12/2003 | Miller |
| 2004/0158173 A1 | 8/2004 | Voegele et al. |
| 2004/0186479 A1 | 9/2004 | Tidwell et al. |
| 2004/0220602 A1 | 11/2004 | Deng et al. |
| 2005/0215921 A1 | 9/2005 | Hibner et al. |
| 2005/0277970 A1 | 12/2005 | Norman et al. |
| 2005/0283150 A1 | 12/2005 | Moutafis et al. |
| 2006/0052790 A1 | 3/2006 | Miller |
| 2006/0200040 A1 | 9/2006 | Weikel, Jr. et al. |
| 2006/0217729 A1 | 9/2006 | Eskridge et al. |
| 2006/0276797 A1 | 12/2006 | Botimer |
| 2007/0016211 A1 | 1/2007 | Botimer |
| 2007/0100362 A1 | 5/2007 | Deng |
| 2007/0156064 A1 | 7/2007 | Ritchart et al. |
| 2007/0179401 A1 | 8/2007 | Hibner |
| 2008/0287925 A1 | 11/2008 | Le et al. |

FOREIGN PATENT DOCUMENTS

| | | |
|---|---|---|
| WO | WO 97-16124 A | 5/1997 |
| WO | WO 2008-144552 | 11/2008 |
| WO | WO 2011-085392 | 7/2011 |

OTHER PUBLICATIONS

International Preliminary Report on Patentability in PCT Application No. PCT/US2011/020884, Jul. 26, 2012, 7 pages.

Communication Pursuant to Rules 161(1) and 162 EPC in corresponding European Application No. 11704502.1, dated Aug. 22, 2012, 2 pages.

Office Action in corresponding European Application No. 11704502.1, dated May 7, 2013, 3 pages.

* cited by examiner

HANDHELD DEVICE WITH THERMAL PADDING

CROSS REFERENCE TO RELATED APPLICATION

This application claims the benefit of U.S. provisional application No. 61/293,986, entitled "HANDHELD MEDICAL DEVICE WITH THERMALLY CONDUCTIVE PADDING," filed on Jan. 11, 2010, the content of which is incorporated by reference herein in its entirety.

BACKGROUND

1. Field

The following disclosure generally relates to handheld devices. More particularly, certain features, aspects and advantages of the following disclosure relate to handheld medical devices having a thermal pad to control the transfer of heat.

2. Description of the Related Art

Handheld medical devices are generally known in which a motor drives a surgical device having any of a number of different functions and operating characteristics. In many cases, the surgical devices are interchangeable such that the same handpiece can be used with any of a number of surgical devices or cutter configurations. In such devices, it is known that excess heat generated by the motor of the device can result in reduced power and/or breakdown of the motor. However, many traditional handheld medical devices are generally not configured to facilitate the transfer of the heat from the motor to other portions of the handheld device and/or to fluid flowing therethrough.

SUMMARY

As disclosed in U.S. patent application Ser. No. 12/122, 400, which is hereby incorporated by reference in its entirety, a handheld medical device can comprise a housing, a motor, and an internal fluid passage extending generally alongside the motor. To enhance the transfer of heat away from the motor, the motor can be partially or completely wrapped with a thermal pad (e.g., a pad that can conduct heat). In some configurations, the pad can be disposed to conduct heat toward the fluid passage, which in turn can be configured to aspirate a fluid in order to transmit the heat from the pad. In some configurations, the pad and/or fluid passage are sized and shaped to transfer an amount of heat to maintain a temperature level of an outer surface of the handheld medical device in accordance with certain industry requirements.

In some embodiments, a medical handpiece comprises a handpiece with a housing having an outer surface and an inner surface. Between the inner surface and the motor can be a gap, which can include an amount of air. In some cases, the thermal pad is disposed between the inner surface and the motor. In some embodiments, the pad is in contact with the inner surface and the motor such that heat can be transferred from the motor, into the padding, and in turn to the inner surface of the housing. In some arrangements, the housing encloses a fluid passage, which can extend generally alongside the elongated motor assembly.

In some arrangements, a medical handpiece comprises: a housing; a motor contained within the housing, the motor configured to drive an implement (e.g., cutter, angled cutter, bur, drill, and the like) or disposed at an end of the housing thereby generating heat; a passage configured to carry a fluid and extending along at least a portion of the motor; and a thermally-conductive pad disposed between the motor and the passage, wherein the thermal conductivity of the pad is greater than the thermal conductivity of air thereby facilitating a flow of heat from the motor to the fluid in the passage. In some embodiments, the thermally-conductive pad is adjacent or in contact with the motor and/or the passage. In some cases, the thermally-conductive pad is configured to transfer a sufficient amount of heat to the fluid in order to maintain the temperature of an outer surface of the housing below a specified upper limit temperature. In some embodiments, the specified upper limit temperature is within the range between about 80 to about 120° Fahrenheit or is set-forth by an industry standard, such as International Electrotechnical Commission standard IEC 60601-1, which is hereby incorporated by reference in its entirety. In some arrangements, the thermally-conductive pad has a thermal conductivity in the range between about 1.0 W/m·K to about 3.50 W/m·K and/or is fiberglass-reinforced silicone gel. In some embodiments, the thermally-conductive pad encircles the motor. In some embodiments, the handpiece is an arthroscopic shaver and/or the implement comprises a blade. In some cases, the passage extends along the entire length of the motor and/or is integral with the housing. Used herein, the term "integral" indicates that components are monolithic or are of unitary construction.

In some embodiments, a medical handpiece comprises: a housing having an inner surface and an outer surface; a motor having a sidewall, the motor disposed in the housing and configured to operate a tool thereby producing heat; a space defined at least in part by the inner surface and the sidewall, the space containing a volume of air; a lumen configured to carry a fluid; and a thermal pad disposed in the space, wherein the thermal conductivity of the thermal pad is greater than the thermal conductivity of air thereby facilitating a flow of heat from the motor to the lumen. In some cases, the thermal pad is adjacent or in contact with the motor and/or lumen. In some arrangements, the thermal pad is configured to transfer a sufficient amount of heat from the motor to the lumen in order to maintain the outer surface of the handpiece below a specified temperature. In some embodiments, at least a portion of the lumen is disposed in the housing. In some cases, the thermal pad has a thermal conductivity in the range between about 1.0 W/m·K to about 3.50 W/m·K and/or comprises fiberglass-reinforced silicone gel.

In some aspects, a method for controlling the temperature of a portion of a medical handpiece comprises: providing a housing having a motor and a passage, the motor configured to drive an implement thereby generating heat, the passage configured to carry a fluid; and providing a thermally-conductive pad between the motor and the passage, wherein the thermal conductivity of the thermally-conductive pad is greater than the thermal conductivity of air thereby facilitating a flow of heat from the motor to the passage, wherein the thermally-conductive pad is configured to transfer a sufficient amount of heat to the passage to maintain the temperature of the portion of the handpiece below a maximum temperature during normal operation of the handpiece. In some embodiments, the thermally-conductive pad is adjacent or in contact with the motor and/or the passage. In some embodiments, the thermal pad has a thermal conductivity in the range between about 1.0 W/m·K to about 3.50 W/m·K and/or the thermal pad comprises fiberglass-reinforced silicone gel.

DETAILED DESCRIPTION

A variety of examples of handheld devices with thermal padding are described below to illustrate various examples that may be employed to achieve desired improvements. These examples are only illustrative and not intended in any way to restrict the general inventions presented and the various aspects and features of these inventions. For example, although embodiments and examples are provided herein in the medical field, the inventions are not confined exclusively to the medical field and certain embodiments can be used in other fields. Furthermore, the phraseology and terminology used herein is for the purpose of description and should not be regarded as limiting. No features, structure, or step disclosed herein is essential or indispensible.

Figure 1:
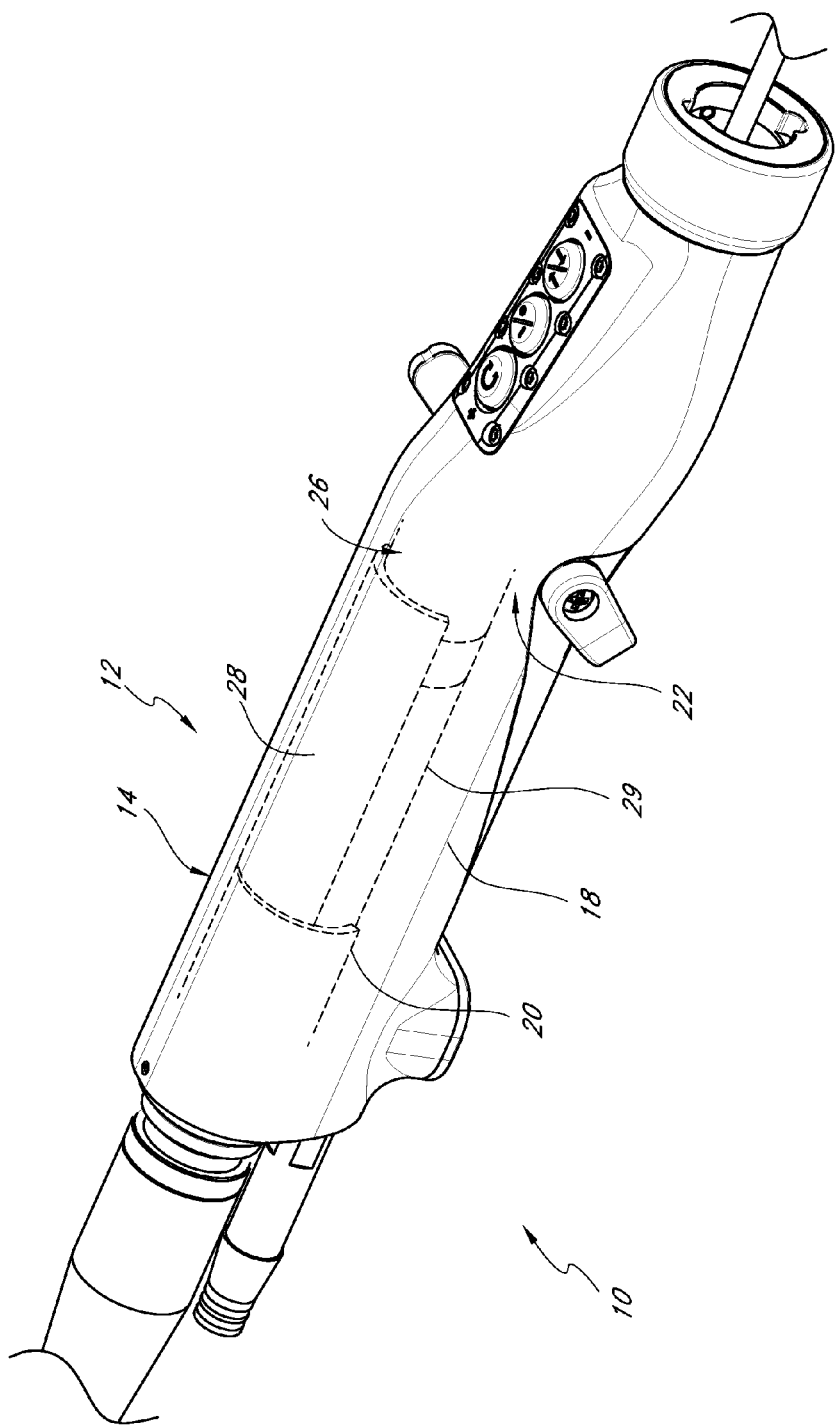
FIG. 1 illustrates a perspective view with cutaways showing an embodiment of an embodiment of handheld medical devices with thermal padding.
Figure 2:
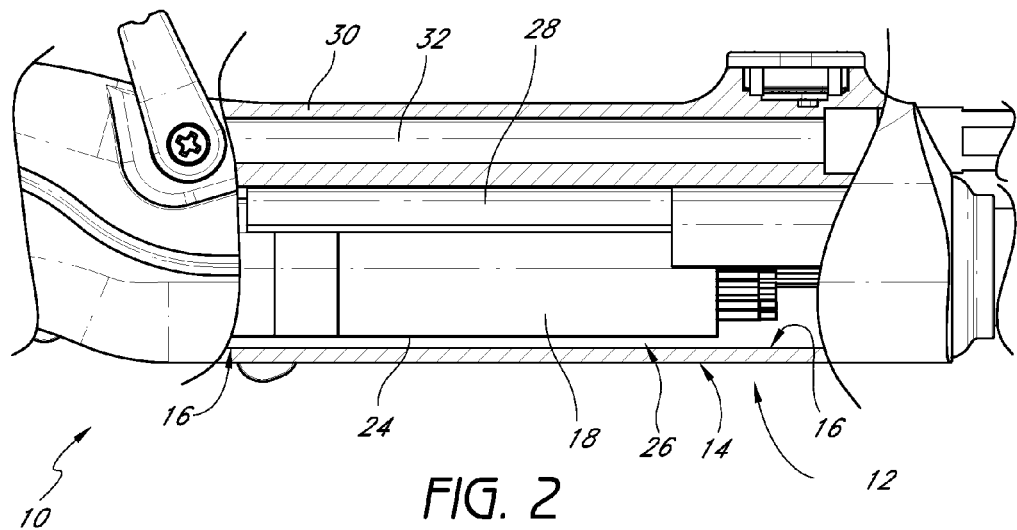
FIG. 2 illustrates a longitudinal cross-sectional view of the device of FIG. 1 with the thermal pad disposed in a non-limiting alternate location.

With regard to FIGS. 1 and 2, embodiments of a handpiece 10 are illustrated. Generally, the handpiece 10 is a medical implement (e.g., arthroscopic shaver) or other type of handheld device that would benefit from any or all of the later described features, aspects and advantages described herein (e.g., handheld rotary drill). The illustrated handpiece 10 has an elongate body and ends having connection points for coupling to an external source, such as electrical power, suction, fluid, or the like. In some embodiments, the handpiece 10 includes one or more handles and/or controls (e.g., buttons, switches, knobs, displays, and the like). The controls can be configured to allow adjustment of one or more parameters of the handpiece 10, such as but not limited to power on/off, direction of operation and/or speed of the implement, direction and/or rate of fluid flow, and the like. In some cases, the handpiece 10 is capable of being autoclaved or otherwise sterilized.

As shown, the handpiece 10 can include a hollow housing 12, a motor 18, a fluid passage 30, and a thermal pad 28 located in a gap 26 between the motor 18 and the housing 12. Many materials (e.g., plastic, metal, resin, composite, combinations thereof, and the like) and forming methods (e.g., injection molding, stamping, forging, casting, machining, curing, combinations thereof, and the like) can be used to form the housing 12.

Normally, the housing 12 is sealed or otherwise generally impervious to liquids. In some embodiments, the housing 12 is a single piece component. In other embodiments, the housing 12 is formed by two or more components that are joined together in any suitable manner (e.g., sonic welding, fasteners, adhesive, combinations thereof, and the like). The illustrated housing 12 is generally an elongate cylinder, though most any shape is possible. In some cases, the housing 12 is shaped to facilitate ergonomic handling and/or manipulation of the handpiece 10.

The motor assembly 18 is generally disposed in the housing 12. Many types of motor assemblies can be used, such as but not limited to air driven, fluid driven, and electric. As shown, the motor includes a proximal end 22, a distal end 20, and at least one sidewall 24. In some cases, the housing 12 contacts and/or supports the motor 18 at one or more of the ends 20, 22. A gap 26 can be located between the motor 18 and an otherwise adjacent but spaced-apart portion of an inner surface 16 of the housing 12 and/or fluid passage (discussed below). In some cases, the gap 26 includes a fluid, such as but not limited to air, nitrogen, helium, oil, and the like.

In some arrangements, a thermal pad 28 is disposed in the gap 26. The thermal pad 28 can extend through some or all of the gap 26. For instance, the illustrated embodiment shows a thermal pad 28 generally extending at least a portion of a longitudinal length of the illustrated motor 18. In another embodiment, the thermal pad 28 fully covers the periphery of the sidewall 24 of the motor 18 and extends the longitudinal length of the motor 18. The thermal pad 28 can comprise one or more layers.

Many sizes and shapes of thermal pad 28 may be employed. In the illustrated configuration, the thermal pad 28 forms at least a portion of a cylinder when installed in the gap 26. In some cases, the pad 28 is generally rectangular when laid flat. For example, the pad 28 can have flat dimensions of about ¾ inch×2 inch×¹⁄₁₆ inch. In another embodiment, when laid flat the pad 28 is rectangular in shape with dimensions of about 1¼ inch×3 inch×⅛ inch. Other embodiments include a thermal pad 28 with alternate dimensions. Still further embodiments include other shapes of thermal pads. For example, in some embodiments the thermal pad 28 is toroidal in shape is configured to encircle at least some of the periphery of the motor 18 and extend along a portion of the longitudinal length of the motor.

The thermal pad 28 normally has a thickness that is the same as or slightly larger than the gap 26. In other words, the thermal pad 28 generally fills the gap or is compressed within the gap. In other arrangements, the thickness of the gap 26 is greater than the thickness of the pad 18, thus permitting a portion of a gap to remain unfilled by the pad 18. In some embodiments, multiple thermal pads are overlapped and/or positioned in varying orientations.

Generally, the thermal pad 28 is constructed of a material that has a thermal conductivity value greater than that of air (e.g., greater than about 0.02 W/m·K). For example, in some aspects the thermal pad 28 has a thermal conductivity of at least 0.05 W/m·K and/or equal to or less than 10.0 W/m·K. In some embodiments, the thermal pad 28 has a thermal conductivity of about 3.50 W/m·K. In some cases, the thermal pad 28 has a thermal conductivity of about 1.3 W/m·K. In some arrangements, the thermal pad 28 has a thermal conductivity of about 1.0 W/m·K. Often, the thermal pad 28 is a fiberglass-reinforced silicone gel. In some embodiments, the thermal pad is a metal (e.g., steel, aluminum, copper, or the like). In some cases, the thermal pad 28 is a TP-3560 THERMAL GAP PAD (commercially available from the Dow Corning Corporation), a GAP PAD 1500S30 (commercially available from The Bergquist Company), or a member of the THERMA-A-GAP™ 500 SERIES (commercially available from the Parker Hannifin Corporation). Normally, the thermal pad 28 is capable of tolerating operating temperatures of the motor 18 under normal and extended use. In some embodiments, the pad 28 can have an adhesive or otherwise tacky side to aid in positioning. In some cases, the thermal pad 28 has a greater thermal conductivity than any other component of the handpiece 10 that is in contact with the motor 18. In some embodiments, the thermal pad 28 has a greater thermal conductivity than the portion of the housing 12 that contacts and/or supports the motor 18.

As the thermal pad 28 has a higher thermal conductivity value than air, heat generated by the motor 18 can be more efficiently conducted through the thermal pad 28 than through air. Accordingly, in a given period of time, a larger quantity heat can be conducted away from the motor 18 when the thermal pad 28 is disposed in the gap 26 than when air alone is disposed in the gap 26. Such positioning of the pad 28 in the gap 26 can thus reduce the total quantity of heat retained by the motor 18, which in turn can facilitate a decrease in incidents of reduced power and/or malfunction of the motor 18.

In some embodiments, the thermal pad 28 can be configured to encourage the flow of heat to a designated region of the handheld device 10. For example, in embodiments with the gap 26 located between the inner surface 16 of the housing 12 and the motor 18, the thermal pad 28 disposed in the gap 26 can facilitate the transfer of heat from the motor 18 to a portion of the housing 12 that is normally not grasped by a user. In some cases, the designated region of the handpiece 10 has fins or the like to facilitate heat transfer to the surrounding environment.

Figure 3:
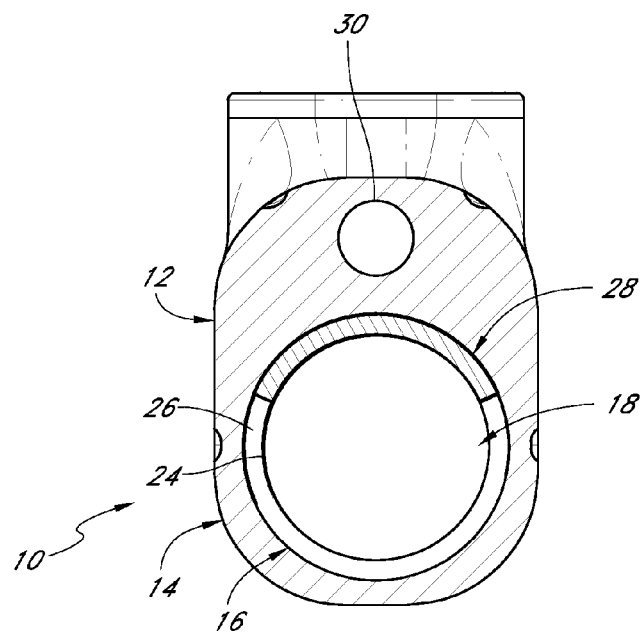
FIG. 3 illustrates a transverse cross-sectional view of the device of FIG. 2.

As shown in FIGS. 2 and 3, the handpiece 10 can include a fluid passage 30, which can be configured to flow a fluid 32 therethrough, such as saline, air, nitrogen, medication, and the like. Generally, the fluid passage 30 is integral with and internal to the housing 12, which can facilitate heat transfer, cleaning, and maintenance. In other configurations, the fluid passage 30 is a separate from and external to the housing 12, such as a hose that extends along and is maintained about adjacent to an outer surface 14 of the housing 12. Often, at least some of the fluid passage 30 extends generally alongside at least a portion of the motor 18.

As illustrated, the gap 26 can be located between the motor 18 and the fluid passage 30 and the thermal pad 28 can be disposed in the gap 26 such that the thermal pad 28 is between the fluid passage 30 and the motor 18. In such a location, the thermal pad 28 can encourage the flow of heat generally from the motor 18 and toward the fluid passage 30. In embodiments with fluid 32 flowing through the fluid passage 30, heat can be transferred to the fluid 32, which can transport the heat away from the motor 18 and the handheld device 10. In some cases, the thermal pad 28 is positioned between the motor 18 and the fluid passage 30 such that the shortest distance from any point on the motor to any point on the fluid passage 30 passes through the thermal pad 28. In some cases, the pad 28 fully encircles at least some of the fluid passage 30.

In some embodiments, the thermal pad 28 and/or the fluid passage 30 can be configured to sustain a temperature of the outer surface 14 of the housing 12 within desired parameters. In some embodiments, the thermal pad 28 and/or the fluid passage 30 are configured so maintain the temperature of the outer surface 14 in accordance with an industry guideline, such as but are not limited to, IEC 60601-1 (available from the International Electrotechnical Commission), UL 60601-1 (available from Underwriters Laboratories Inc.), or similar, each of which is incorporated by reference herein in the entirety. For instance, the material, size, shape, and location of the thermal pad 28 in the gap 26 can be configured to transfer heat from the motor 18 to the fluid passage 30 thereby preventing undesired heat transfer to housing 12 and facilitating the maintenance of a temperature of at least a portion of the outer surface 14 of the housing 12 within a desired range (e.g., about 60 to about 140° F., about 80 to about 120° F., less than about 130° F., about 150° F. maximum, etc.). In some arrangements, if the temperature of the outer surface 14 of the housing 12 exceeds a desired value, the handpiece 10 becomes disabled and/or enters a reduced operation state (e.g., at less than full power) until the temperature is below the desired value.

Although the foregoing description and summary have been disclosed in the context of aspects of certain preferred embodiments, examples and variations, it will be understood by those skilled in the art that the present invention extends beyond the specifically disclosed embodiment and variation to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. Thus, it is intended that the scope of the invention herein disclosed should not be limited by the particular disclosed embodiments described above, but should be determined only by a fair reading of the claims that follow.

What is claimed is:

1. A medical handpiece, comprising:
a housing including an outer surface;
a motor contained within the housing, the motor configured to drive an implement disposed at an end of the housing thereby generating heat;
a passage configured to carry a fluid and extending along at least a portion of the motor; and
a thermally-conductive pad disposed between the motor and the passage, wherein the thermal conductivity of the pad is greater than the thermal conductivity of air thereby facilitating a flow of heat from the motor to the fluid in the passage;
wherein the thermally-conductive pad is configured to transfer a sufficient amount of heat to the fluid in order to maintain a temperature of at least a portion of the outer surface below a specified upper limit temperature.

2. A handpiece according to claim 1, wherein the specified upper limit temperature is the range between about 80 to about 120° Fahrenheit.

3. A handpiece according to claim 1, wherein the specified upper limit temperature is set-forth by International Electrotechnical Commission standard IEC 60601-1.

4. A handpiece according to claim 1, wherein the thermally-conductive pad has a thermal conductivity in the range between about 1.0 W/m·K and about 3.50 W/m·K.

5. A handpiece according to claim 1, wherein the thermally-conductive pad comprises fiberglass-reinforced silicone gel.

6. A handpiece according to claim 1, wherein the thermally-conductive pad encircles the motor.

7. A handpiece according to claim 1, wherein the passage extends along the entire length of a casing of the motor.

8. A handpiece according to claim 1, wherein the passage is integral with the housing of the medical handpiece.

9. A handpiece according to claim 1, wherein the handpiece is an arthroscopic shaver and the implement comprises a blade.

10. A handpiece according to claim 1, wherein the thermally-conductive pad is in contact with both the motor and the passage.

11. A medical handpiece, comprising:
a housing having an inner surface and an outer surface;
a motor having a sidewall, the motor disposed in the housing and configured to operate a tool thereby producing heat;
a space defined at least in part by the inner surface and the sidewall, the space containing a volume of air;
a lumen configured to carry a fluid; and
a thermal pad disposed in the space and having a thermal conductivity greater than the thermal conductivity of air thereby facilitating a flow of heat from the motor to the thermal pad, wherein the thermal pad is configured to transfer a sufficient amount of heat to the lumen in order to maintain at least a portion of the outer surface of the handpiece below a specified temperature.

12. A handpiece according to claim 11, wherein at least a portion of the lumen is disposed in the housing.

13. A handpiece according to claim 11, wherein the thermal pad has a thermal conductivity in the range between about 1.0 W/m·K and about 3.50 W/m·K.

14. A handpiece according to claim 11, wherein the thermal pad comprises fiberglass-reinforced silicone gel.

15. A method for controlling the temperature of a portion of a medical handpiece, comprising:

providing a housing having a motor and a passage, the motor configured to drive an implement thereby generating heat, the passage configured to carry a fluid; and providing a thermally-conductive pad between the motor and the passage, wherein a thermal conductivity of the thermally-conductive pad is greater than a thermal conductivity of air thereby facilitating a flow of heat from the motor to the passage, wherein the thermally-conductive pad is configured to transfer a sufficient amount of heat to the passage to maintain a temperature of at least a portion of the handpiece below a maximum temperature during normal operation of the handpiece.

16. A handpiece according to claim 15, wherein the thermal pad has a thermal conductivity in the range between about 1.0 W/m·K and about 3.50 W/m·K.

17. A handpiece according to claim 15, wherein the thermal pad comprises fiberglass-reinforced silicone gel.

* * * * *